Figure 1:
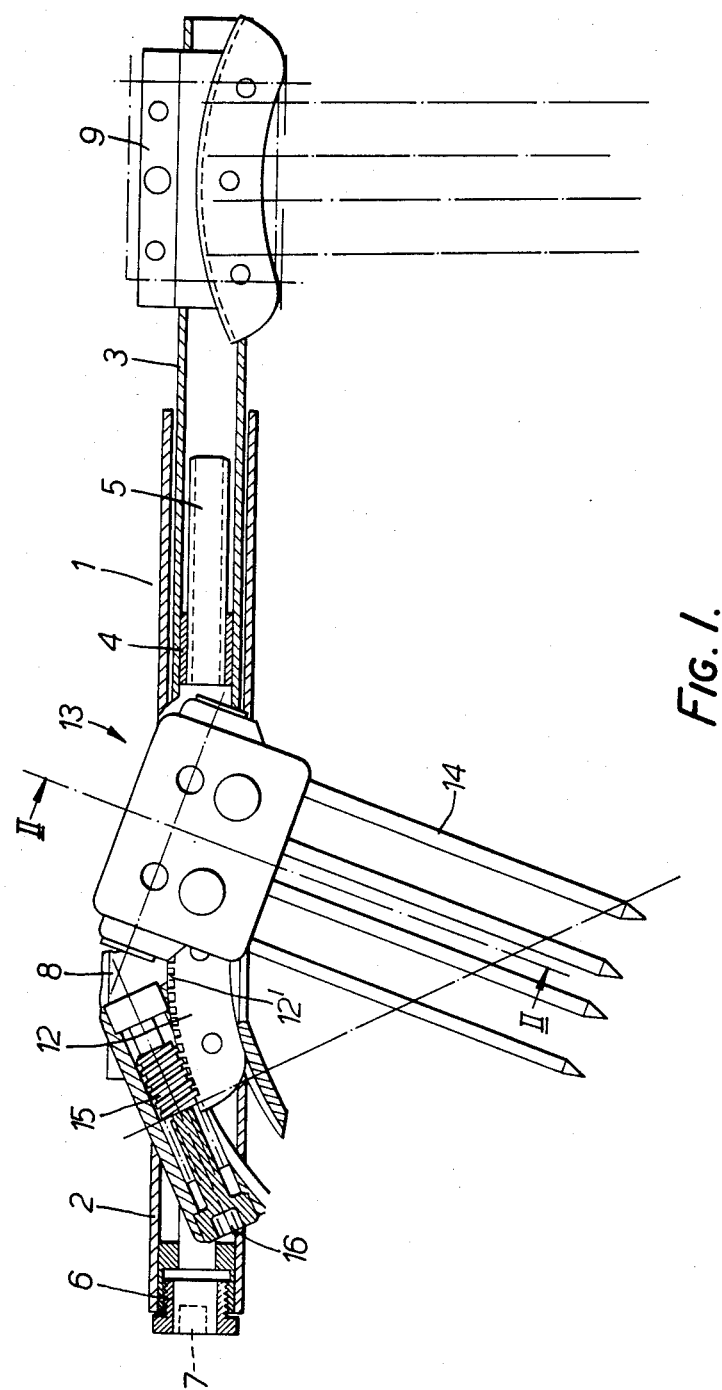

United States Patent [19]

Helland

[11] Patent Number: 4,488,542

[45] Date of Patent: Dec. 18, 1984

[54] EXTERNAL SETTING AND CORRECTION DEVICE FOR THE TREATMENT OF BONE FRACTURES

[76] Inventor: Per Helland, Astrids vei 43, 4600 Kristiansand S, Norway

[21] Appl. No.: 441,994

[22] Filed: Nov. 16, 1982

[30] Foreign Application Priority Data

Nov. 27, 1981 [NO] Norway ................................. 814051

[51] Int. Cl.³ .......................... A61F 5/04; A61B 17/18
[52] U.S. Cl. ................................ 128/92 A; 128/84 B; 128/92 E
[58] Field of Search ................... 128/92 A, 92 R, 92 E, 128/84 R, 84 B

[56] References Cited

U.S. PATENT DOCUMENTS

| 2,250,417 | 7/1941 | Ettinger | 128/92 A |
| 2,333,033 | 10/1943 | Mraz | 128/92 A |
| 2,391,537 | 12/1945 | Anderson | 128/84 B |

FOREIGN PATENT DOCUMENTS 2457676  1/1981  France ................................ 128/92 A

*Primary Examiner*—Ronald L. Frinks
*Attorney, Agent, or Firm*—Ladas & Parry

[57] ABSTRACT

A device for external correction and setting of the bone parts at the site of a fracture, comprising a rigid rod, adjustable in length, with two holders which carry a plurality of transcutaneous pins. Each of the holders is rotatable in two planes that are disposed at right angles relative to each other. On each holder an arc-shaped guide is provided in a plane parallel to the axis of the rod. Each guide has a radius which approximately corresponds to the presumed distance between the center of the bone and the arc-shaped guide. The arc-shaped guides are provided with worm wheel teeth, and a worm is mounted in each of the holder parts for engagement with the teeth. Each of the holders is a two-part assembly, having a first part fastened to the rod above the arc-shaped guide and a second part carrying the pins and rotatably connected to the first part about an axis of rotation disposed at a right angle in relation to the axis of the curved guide. The pins are disposed at an acute angle in relation to the axis of rotation of the second part of the holder. The centerlines of the pins intersect said axis of rotation at the latter's point of intersection with the axis of the arc-shaped guide.

7 Claims, 14 Drawing Figures

FIG. I.

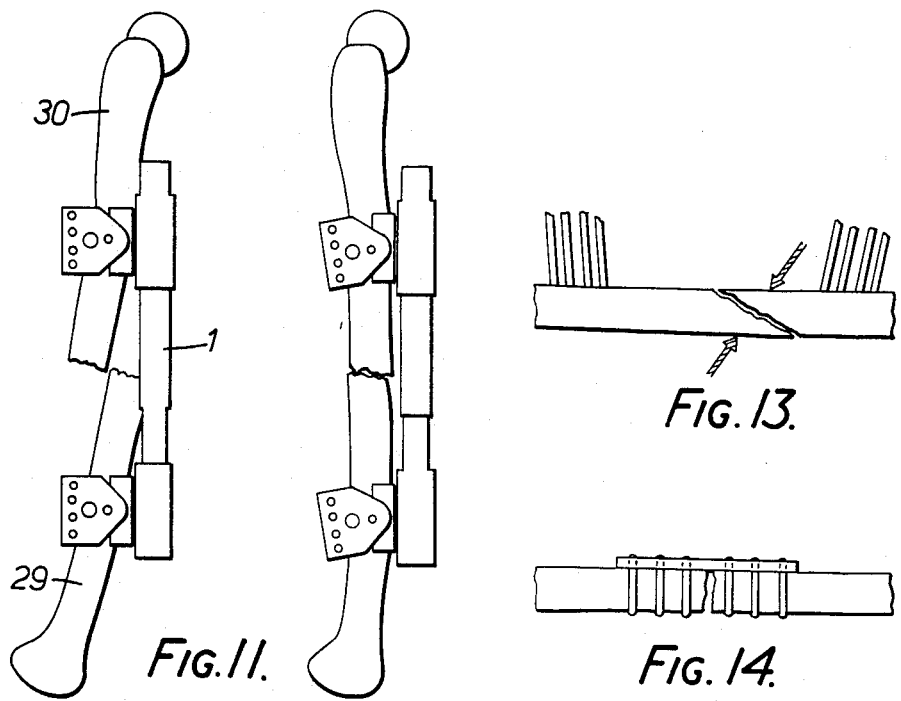
FIG. 11.
FIG. 13.
FIG. 14.
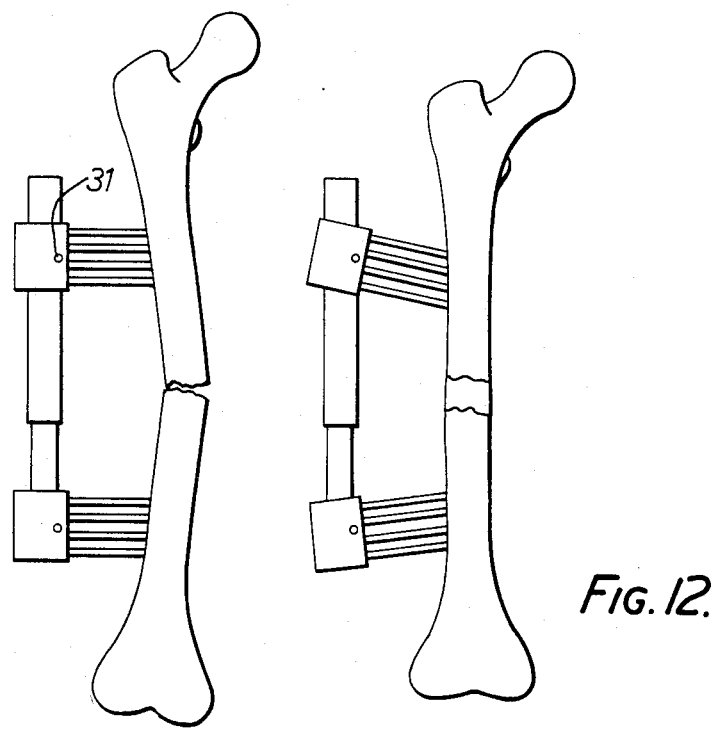
FIG. 12.

EXTERNAL SETTING AND CORRECTION DEVICE FOR THE TREATMENT OF BONE FRACTURES

The present invention relates to a device for the external setting and correction of a broken bone at the site of a fracture, comprising a rigid rod, adjustable in length, intended during use to lie outside the skin, and two holders fastened to the rod and carrying a plurality of transcutaneous pins which are intended to penetrate the skin and muscle tissue around the fracture site so that the threaded free ends of the pins may be secured in holes bored in the bone parts, the pins of one holder entering the bone above the fracture and the pins of the other holder below the fracture, the holders being rotatable about two axes disposed at an angle relative to each other.

In general, and somewhat simplified, one may say that bones are corrected and set by three different methods when treating a fracture (and in osteotomies). These three methods are:

1. External bandaging—usually plaster casts.
2. Internal fastening means, which are inserted during a surgical operation and enclosed within the patient's body. Such means include screws, plates or rails with screws, marrow nails, pins, wires, etc.
3. Pins passing through the skin and soft tissues into the bone, and some kind of external connection between the pins which are positioned in the bone parts above and below the fracture. The external connection may be flat or polygonal in shape.

The present invention relates to the latter method of treatment.

In bone fractures, the malpositions which have to be corrected fall into the following categories:

1. Relative angle misplacement of the bone parts. The angular malposition may be in any direction.
2. Parallel displacement.
3. Rotational displacement.
4. Longitudinal displacement.

A number of devices for external corrections and setting of broken bones have been proposed, and some are available on the market. The transcutaneous pins can be positioned at an angle in two planes for effecting the necessary correction. Thus, an angular misplacement in any direction can be corrected. In the prior art devices, however, the center of rotation for the pins is located in the pin holder; the outer ends of the pins will describe an arc, and a longitudinal displacement of the bone parts will occur. This is a drawback for two reasons: First, when correcting an angular malposition, the bones may become displaced longitudinally, and this will have to be corrected subsequently; and second, considerable forces are operative in the longitudinal direction of the bone which must be overcome when correcting the angle since the bones must simultaneously be moved longitudinally.

An external device of the above type is disclosed in U.S. Pat. No. 2,250,417. This device comprises a rod with two holders for the transcutaneous pins, wherein one of the holders can be moved along the rod and secured in the desired position relative to the rod. The center of rotation for the pins, in both planes, is located in the holder, and the outer ends of the pins will describe an arc so that a longitudinal displacement of the bones occurs. Rotational correction is performed through the provision in the pin holders of a curved guide lying in a transverse plane in relation to the axis of the rod, the guide being made as a curved rack. Two pinion wheels mounted on the rod engage with the teeth on the rack. As the pinion wheels are rotated, the arc-shaped guide will move about a center which is located in the center of the bone when the device is in use.

The primary object of the present invention is to eliminate the above-mentioned drawback, thus permitting one to correct each malposition separately and in a controlled fashion without disturbing the outer corrections. Moreover, it is desired to provide a device of the above type which requires little space, because the patient, after the necessary corrections and setting have been accomplished, is supposed to wear the device until the break has healed. It is a further object of the invention to provide an external bone setting device with which it is possible—if desired—to release the bones from the longitudinal setting while retaining the other settings. External forces will then be transmitted to the ends of the bone at the break, and alternating compression of this type at the fracture site is thought to stimulate the growth of new bone. In addition, the present invention is formed in such a way that it is easy to compress and post-operatively compress a diagonal break.

The above objects are obtained in the invention with a device for external correction and setting of the bone parts at the side of a fracture, comprising a rigid rod, adjustable in length, which during use is intended to lie outside the skin, and two holders fastened to the rod which carry a plurality of transcutaneous pins that are intended to penetrate the skin and muscle tissue around the site of the fracture so that the free ends of the pins can be secured in holes bored in the bone parts, the pins of one holder entering the bone above the fracture and the pins of the other holder below the fracture, each holder being rotatable in two planes disposed at right angles relative to each other. This device is characterized in that on each of the holders, an arc-shaped guide is provided in a plane parallel to the axis of the rod, that each guide has a radius which approximately corresponds to the presumed distance between the center of the bone and the arc-shaped guide, that on the convex surface of the arc-shaped guides, which faces away from the pins, the guide is provided with worm wheel teeth, that a worm is mounted on each of the holders for engagement with the teeth on the guide, that each of the holders is composed of two parts, a first part fastened to the rod above the arc-shaped guide and a second part carrying the pins and rotatably connected to the first part about the axis of rotation disposed at a right angle in relation to the axis of the arc-shaped guide, and that the pins are disposed at an acute angle relative to the axis of rotation of the second part of the holder, the centerline of the pins intersecting said axis of rotation at its point of intersection with the axis of the arc-shaped guide.

A preferred embodiment of the invention is characterized in that the rod, as known per se, is telescopically adjustable in length, that an inwardly directed screw spindle is rotatably mounted within one telescoping member and engages with a fixed nut within the other telescoping member, and that the spindle can be released from engagement with the nut.

In a further feature of the invention, the second (outer) telescoping member has two lugs which surround the first (inner) member.

A practical embodiment of the invention is characterized in that the two holders are fastened to the rod by means of easily detachable clamp fasteners.

To enable rotational correction of the bones, the invention provides that at least one of the clamp fasteners is rotatable on the rod.

The invention will be explained in greater detail in the following with reference to the accompanying drawings, which show an embodiment of the invention together with a number of illustrations showing utilization of the device.

Figure 2:
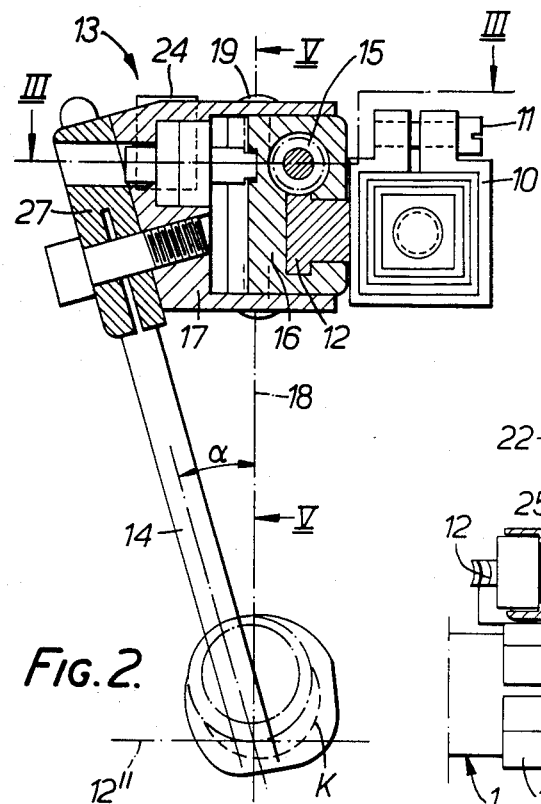
Figure 3:
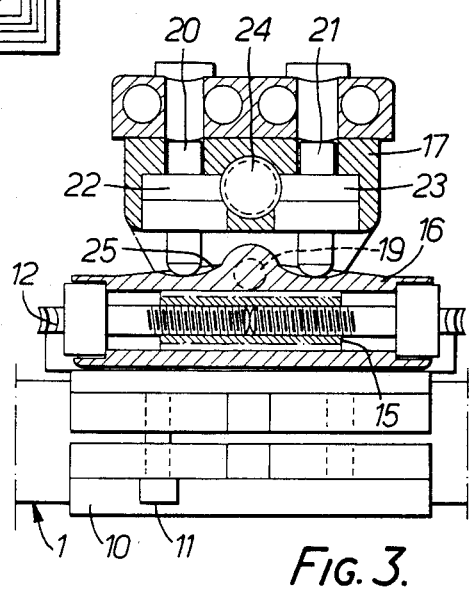
Figure 4:
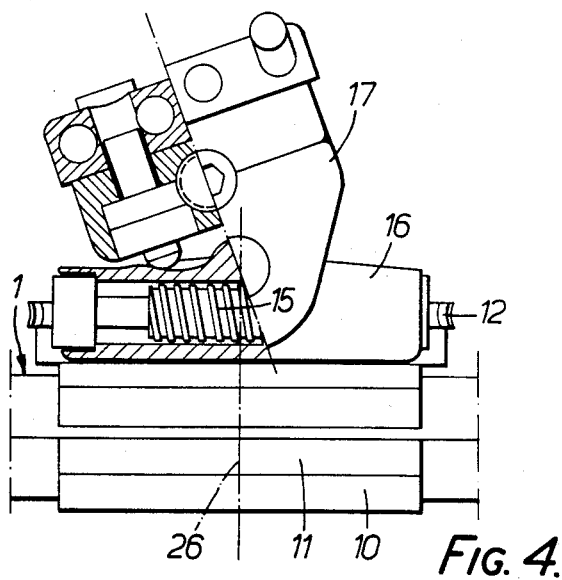
Figure 5:
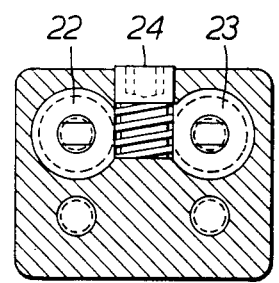
Figure 6:
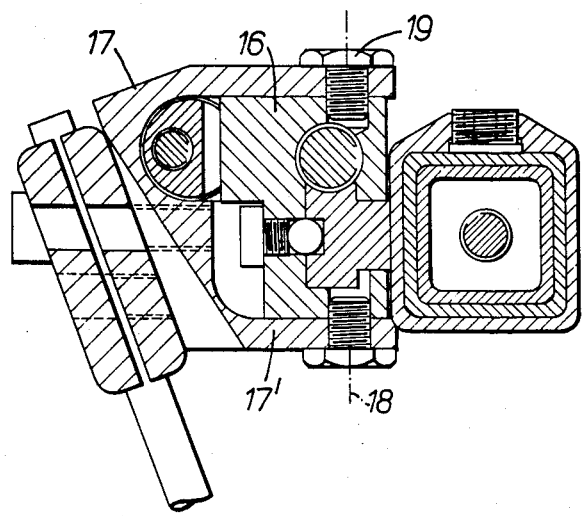
Figure 7:
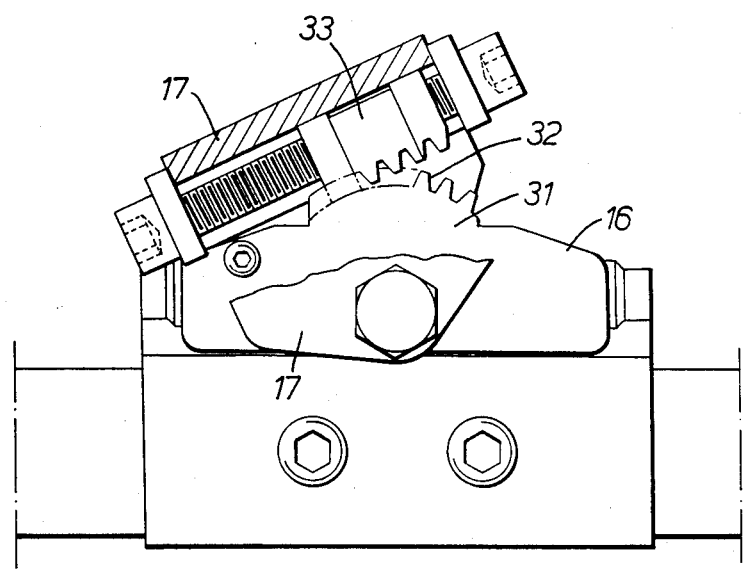
Figure 8:
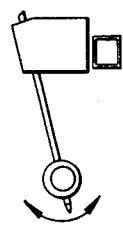
Figure 9:
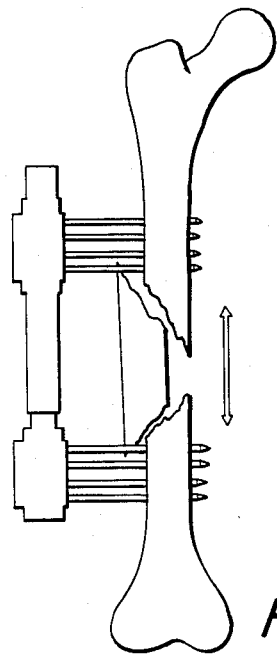

FIG. 1 is a somewhat schematic drawing of an embodiment of the device according the the invention, FIG. 2 is a cross section along the line II—II in FIG. 1, FIG. 3 is a cross section along the line III—III in FIG. 2, FIG. 4 shows a holder in a different position than in FIG. 3, FIG. 5 is a cross section along the line V—V in FIG. 2, FIG. 6 shows an alternative embodiment of a holder, in cross section, FIG. 7 shows the holder of FIG. 6 seen from above and in partial cross section, FIG. 8 is a schematic illustration of the device during use, seen from the end, FIG. 9 shows the device in use for correcting a double fracture of the femur, where a longitudinal displacement is necessary.

Figure 10:
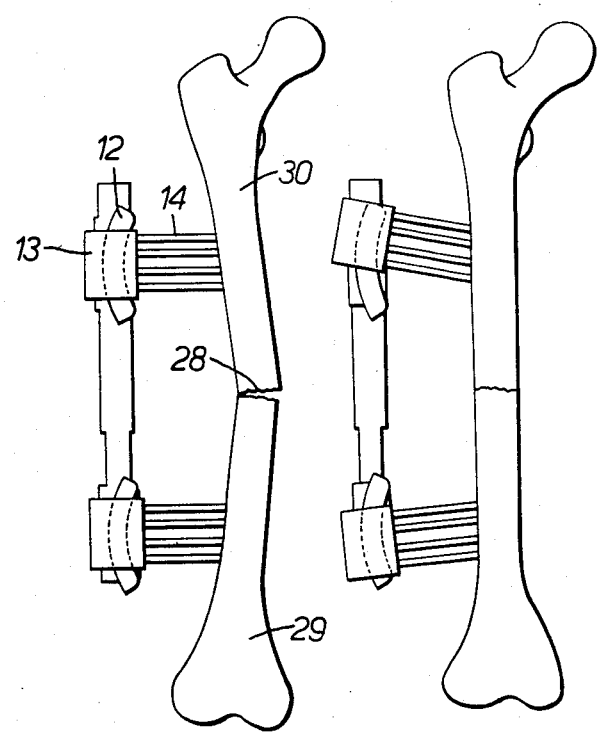

FIG. 10 shows the device in use for correcting the angle in a simple fracture of the femur, FIG. 11 shows the device in use for correcting a parallel displacement condition, FIG. 12 illustrates how an earlier device would work for correction of an angular malposition, FIG. 13 schematically illustrates how a diagonal break can be compressed, and FIG. 14 shows how a distance (diastasis) may occur which prevents healing of the break when a fracture is treated with internal means.

The device consists of an extensible rod 1 composed of two telescoping square tubes 2, 3. A nut 4 is fastened in the tube 3 and engages with a threaded spindle 5 which is rotatably mounted at the end of the tube 2. At this end, the spindle has a head 6 with a groove 7 for operation by, for example, a hexagon wrench. The head 6 can be released by screwing off the sleeve surrounding the head, whereby the spindle 5 can move freely in and out of the rod 1. On each of the tubes 2 and 3 there is a movable holder 8, 9, fastened to the tubes with screws 11. Secured to each of the holders 8, 9 is an arc-shaped guide 12 with worm wheel teeth 12', the axis 12" thereof lying 60-70 mm below the central axis of the rod 1. Provided on the curved guide 12 is a movable head 13, in which four transcutaneous pins 14 are fastened. The position of the head 13 in relation to the worm teeth 12' may be adjusted by means of a self-locking worm 15 operated by the surgeon with a wrench inserted into a groove 16 at the free end of the screw.

The head 13 is divided into two main parts. A base member 16 guided onto the curved guide 12, and a fork-like outer bracket 17 with lugs 17' is hinged to the base member 16. The outer bracket is hinged to the base member 16 about an axis 18 by means of hinge pins 19 passing through the lugs 17'.

The pins 14 are fastened to a pin retainer 27 which is secured in easily detachable manner to the bracket member 17. The purpose of this is to allow the pin retainer and pins to be separated from the rest of the correction device after a desired correction has been performed. The two pin retainers 27 with pins 14 may be fastened e.g., by means of a lockable ball joint to a simple telescoping rod. The entire device, apart from the pin retainers 27 with the pins 14, can thereby be removed for use by other patients. The patient under treatment then has a far smaller and lighter-weight device which is more comfortable to wear.

In the embodiment illustrated in FIGS. 1–5 the angular position of the bracket members 17 is adjusted by means of a worm 24 which can be operated by a hexagon wrench, for instance. The worm 24 engages with two oppositely rotating worm wheels 22, 23 which are rotatably mounted in the bracket member 17. Each of the two worm wheels 22, 23 is provided with a threaded central bore which is in engagement with threaded screws 20, 21. When the worm 24 is operated, therefore, the screws 20, 21 will move in opposite directions. The tips of the screws 20, 21 are rounded and cooperate with curved guides in the base member 16. By means of this device, the bracket member 17 with the pins 14 can be adjusted about 20°–25° in both directions from a neutral position about the axis 18.

In the embodiment illustrated in FIGS. 6 and 7, the bracket member 17 is similarly mounted on the base member 16 by means of lugs 17' and hinge pins 19. The mechanism for permitting movement of the bracket 17 in relation to the base 16 consists of a curved guide 31 with worm wheel teeth 32, engaging with a worm 33 which is mounted in the bracket. When the worm is operated, the bracket 17 can be moved in both directions from a neutral plane about the axis 18.

When the surgeon turns a correction screw 15 or 24, he alters the angle between the bone and the rod 1 in one of the two planes which are parallel to the sides of the square tube, and it is thus easy for the surgeon to imagine or observe what is taking place. It is this condition only which the surgeon changes when performing a correction. By separating the correction functions as is done with the device of the invention, the correction work is made simpler and is more precise. For correcting an angle (see FIG. 10), the correctiion will have to be performed about the axis 26 by means of one correction screw 15 in both holders, both above and below the fracture 28. The lower holder head 13 is for instance moved downwardly along the curved guide to a position as shown in the right-hand figure, and the upper holder head 13 is moved upwardly, and one thereby effects a change in the angle between the bone parts 29 and 30 without any longitudinal displacement of the bone parts. In a similar manner, one can correct a parallel displacement (FIG. 11) by adjusting both screws 24, thereby adjusting both brackets 17 so that the broken end of the lower bone part 29 is moved away from the rod 1 while the broken end of the upper bone part 30 is moved inwardly, until the ends lie in contact with each other as shown in the right-hand drawing in FIG. 11.

FIG. 12 shows how an angular malposition will be corrected with the devices known heretofore, where the holders are rotatable about a center 31 at the extensible rod. When the pin holders are rotated to correct the angle, this will cause a longitudinal displacement of the bone members. This longitudinal displacement will impart very great forces to the correcting device.

The pins 14 are secured to the outer bracket 17 so that they point diagonally downwards, and the axis of the pins intersects the center of the axis of correction 18 at the center of the bone B (see FIG. 2). In the same manner, the axis of correction 26 for the curved tooth member is located at the center of the bone. The center for the movements of the movements of the bone during corrections in the two planes, in other words, is the point of intersection between the bone and the transcutaneous pins. The main idea is that the center for the adjusting movement is located in the bone, 60–70 mm away from the rod 1. If there is deviation from this distance, a longitudinal displacement will occur, but it will be substantially reduced as compared to the situation in which the center is located at the rod 1. This is very important especially in connection with correcting fractures which have partially begun to grow, since such fractures resist longitudinal changes more than angular changes. Longitudinal displacement in the form of shortening will naturally also be impossible if the bone ends stand butt-to-butt in a transverse break. Such placement will then block and prevent the correctional work if the previously known devices are used (FIG. 12).

Owing to the above condition, that the center of correction is located in the bone, forces operating in the longitudonal direction of the bone or break will not affect the correction screws. This makes it possible to use smaller-dimension components in the correction devices. At the same time, the devices will still allow the patient to put weight on the broken member, even in the case of very unstable fractures.

The device of the invention provides a solution which can be made to take up little space, because small forces are operative during the corrections.

Angular or parallel displacements will usually lie in a plane which more or less departs from the plane of the square rod, and all four adjustment screws 15 and 24 will have to be used for correction. This may sound complicated, but in view of the fact that the individual malpositions can be corrected separately without disturbing the other corrections, this is an advance in relation to existing devices, where one has to loosen and fasten universal connections and everything gets out of control. As mentioned above, another advantage of the device is that one can exert great force in the correction movement.

Moreover, one can adjust the angle in a controlled manner a predetermined number of degrees. About 4° angular correction/revolution of the correction screws 15 and 24 is aimed for.

With this device, it is possible to compress and post-operatively compress diagonal breaks. Compressive forces can be applied by means of the correction screws in the two holders, as shown in FIG. 11. The elasticity in the system maintains a biasing force, which also can be utilized to prevent shortening.

Post-operative corrections in the hospital bed and under ambulatory or polyclinical control and follow-up treatment are possible. With the aid of the device, one could compress the break gradually and in a controlled manner in the longitudinal direction when the bones have partially grown together, and can apply post-operative compressive forces to simple transverse fractures which have been subjected to compression from the beginning.

The device of the invention is well suited for ambulatory treatment or follow-up treatment, which is important since this frees hospital beds.

The invention is not restricted to the embodiment shown and the utilization described above. The same system can be utilized for treating fractures other places in the skeleton. The embodiment illustrated herein may also be modified in certain details without departing from the appurtenant patent claim. (Thus, for example, one or both holders can be adjustable about the longitudinal axis of the rod, for performing minor corrections of rotational displacement). In addition, the telescopic tubes can be provided with surfaces facilitating mutual sliding of the parts, e.g., plastic to metal. The screw for longitudinal correction of the rod can also be made so that in addition to being used for traction and compression, it could also be easily detached to allow the alternating "natural" longitudinal forces from the muscles and loads to operate on the fracture, while still retaining the set in other respects. This stimulates the growth of new bone.

Having described my invention, I claim:

1. A device for external correction and setting of bone parts at the site of a fracture, comprising a rigid rod, adjustable in length, intended during use to lie outside the skin, and two holders fastened to the rod and carrying a plurality of transcutaneous pins which are intended to penetrate the skin and muscle tissue around the fracture site so that the free ends of the pins may be secured in holes bored in the bone parts, the pins of one holder adapted for entering the bone above the fracture and the pins of the other holder adapted for entering below the fracture, each holder being rotatable in two planes disposed at right angles to each other, characterized in that on each of the holders an arc-shaped guide is provided in a plane parallel to the axis of the rod, that each guide has a radius which approximately corresponds to the presumed distance between the center of the bone and the arc-shaped guide, that on the convex surface of the curved guide, facing away from the pins, the guide is provided with worm wheel teeth, that a worm is mounted on each of the holder parts for engagement with the teeth on the guide, that each of the holders is composed to two parts, a first part being fastened to the rod above the arc-shaped guide and a second part supporting the pins and rotatably connected to the first part about an axis of rotation disposed at a right angle relative to the axis of the arc-shaped guide, and that the pins are disposed at an acute angle in relation to the axis of rotation of the second holder part, the centerlines of the pins intersecting said axis of rotation at the latter's point of intersection with the axis of the arc-shaped guide.

2. A device according to claim 1, characterized in that the rod, in a manner known per se, is telescopically adjustable in length, that an inwardly directed screw spindle is rotatably mounted within one telescoping member and is in engagement with a fixed nut mounted within the second telescoping member, and that the spindle can be released from engagement with the nut.

3. A device according to claim 1, characterized in that the second (outer) holder part has two lugs which surround the first (inner) holder part.

4. A device according to claim 1, characterized in that the two holders are secured to the rod by easily detachable clamp fasteners.

5. A device according to claim 4, characterized in that at least one clamp fastener is rotatably disposed on the rod.

6. A device according to claim 1, characterized in that the telescoping members consist of a polygonal tube, e.g., a square tube, and that a slide guide or slide coating is provided between the two telescoping parts, for example steel against plastic, of obtaining no-play, low-friction sliding movement of one part relative to the other.

7. A device according to claim 1, characterized in that an arc-shaped guide is provided on each of the holder parts in a plane that is perpendicular relative to the plane of the arc-shaped guide, the convex surface of said guide facing toward the holder part and having worm wheel teeth, and that a worm is mounted in the holder part and is in engagement with the teeth.

* * * * *